United States Patent
Wu et al.

(10) Patent No.: US 9,116,113 B2
(45) Date of Patent: Aug. 25, 2015

(54) SENSING METHOD OF ELECTROCHEMICAL SENSOR

(71) Applicant: I-SHOU UNIVERSITY, Kaohsiung (TW)

(72) Inventors: Jau-Yann Wu, Kaohsiung (TW); Shih-Han Wang, Kaohsiung (TW)

(73) Assignee: I-SHOU UNIVERSITY, Kaohsiung (TW)

( * ) Notice: Subject to any disclaimer, the term of this patent is extended or adjusted under 35 U.S.C. 154(b) by 177 days.

(21) Appl. No.: 13/726,632

(22) Filed: Dec. 26, 2012

(65) Prior Publication Data
US 2014/0042036 A1      Feb. 13, 2014

(30) Foreign Application Priority Data
Aug. 10, 2012 (TW) .............................. 101129049 A

(51) Int. Cl.
G01N 27/327 (2006.01)
G01N 27/30 (2006.01)
G01N 33/52 (2006.01)

(52) U.S. Cl.
CPC .......... *G01N 27/305* (2013.01); *G01N 27/3277* (2013.01); *G01N 33/52* (2013.01)

(58) Field of Classification Search
None
See application file for complete search history.

(56) References Cited

U.S. PATENT DOCUMENTS

| | | | |
|---|---|---|---|
| 5,320,725 A | 6/1994 | Gregg et al. | |
| 5,866,353 A | 2/1999 | Berneth et al. | |

FOREIGN PATENT DOCUMENTS

| | | |
|---|---|---|
| CN | 101255261 | 9/2008 |
| TW | I300478 | 9/2008 |
| TW | 201040528 | 11/2010 |

OTHER PUBLICATIONS

G. Wang, et al. "Fluorescent Si nanoparticle-based electrode for sensing biomedical substances" Optics Communications, vol. 281, 2008, p. 1765-1770.*
Y. Choi, et al. "Electro-oxidation of organic fuels catalyzed by ultrasmall silicon nanoparticles" Applied Physics Letters, vol. 93, paper No. 164013, 2008, p. 164103-1-164103-3.*
Wang et al., "Fluorescent Si nanoparticle-based electrode for sensing biomedical substances," Optics Communications, 2008, pp. 1765-1770.
"Office Action of Taiwan Counterpart Application", issued on May 20, 2014, p. 1-p. 4, in which the listed references were cited.

* cited by examiner

*Primary Examiner* — J. Christopher Ball
(74) *Attorney, Agent, or Firm* — Jianq Chyun IP Office

(57) ABSTRACT

A sensing method of an electrochemical sensor including the following steps is provided. First, a fluorescent material is immobilized on a surface of an electrode so as to form a sensing electrode. The sensing electrode is then used to execute an electrochemical test of a target in a light-shielding environment.

9 Claims, 4 Drawing Sheets

SENSING METHOD OF ELECTROCHEMICAL SENSOR

CROSS-REFERENCE TO RELATED APPLICATION

This application claims the priority benefit of Taiwan application serial no. 101129049, filed on Aug. 10, 2012. The entirety of the above-mentioned patent application is hereby incorporated by reference herein and made a part of this specification.

TECHNICAL FIELD

The disclosure relates to a sensing method of an electrochemical sensor, and also relates to a sensing method of an electrochemical sensor with desirable sensitivity.

BACKGROUND

In recent years, the aging population increases. Hence, the medical sensing technology becomes more important for early discovery of any physical disorder or illness and a proper treatment thereof. The so-called biosensor refers to an analytical apparatus in which biomolecules (such as enzyme, antibody, etc.) react with a target (such as glucose, potassium ions, cholesterol, DNA, tumor markers, etc.) in a system, and the reaction result is converted to an electronic, optical, thermal, magnetic or wave signal. The major components of a biosensor include a biosensing material, a transducer and an electronic device. A biosensor employs a highly selective biosensing material to react with the target (analyte), transmits the reaction results in a form of an optical, electrical, thermal, magnetic, or wave signal via a transducer, and displays the results with the associated electronics or data processors. Typically, biosensors are divided into enzymatic sensors, immuno sensors, and chemical receptor sensors, etc., based upon the sensitive biological material used. For example, a specific enzyme is used to catalyze the reaction of the targeted analyte, and the corresponding response is properly transformed with a transducer and displayed on the reader device in the system of enzymatic sensor. The structure of a biosensor is more compact than conventional analytic instruments and is easily portable and is more friendly to use. Hence, patients or any users, whenever it is necessary, may use the simple detection method at home to monitor the instant status of a physical condition.

Most of commercially available biosensors employ electrochemical sensing mode for its simple operation, high sensitivity, and reasonable cost. Enzymatic sensor, in which oxidases and dehydrogenases are frequently employed, is one of the most commonly used electrochemical biosensors. Hydrogen peroxide ($H_2O_2$) and reduced β-nicotinamide adenine dinucleotide (NADH) are the common co-products of reactions catalyzed by oxidases and dehydrogenases respectively. Consequently, the levels of $H_2O_2$ and NADH are often measured to indicate the level of analytes. Therefore, sensors with high sensitivity to $H_2O_2$ or NADH imply a great opportunity for biosensors with oxidases or dehydrogenases, respectively.

SUMMARY OF THE DISCLOSURE

An exemplary embodiment of the disclosure provides a sensing method of an electrochemical sensor, wherein the sensing method has a higher sensitivity.

An exemplary embodiment of the disclosure provides a sensing method of an electrochemical sensor, which includes at least the following process steps. A fluorescent material is immobilized on a surface of an electrode to form a sensing electrode. Then, in a light-shielding environment, an electrochemical test is performed on a target using the sensing electrode.

According to an exemplary embodiment of the disclosure, the above fluorescent material includes quinine hemisulfate, in which the major source of fluorescence is quinine.

According to an exemplary embodiment of the disclosure, the above fluorescent material includes an oligochitosan fluorescent derivative.

According to an exemplary embodiment of the disclosure, the above fluorescent material includes a polyethylene imine (PEI) fluorescent derivative.

According to an exemplary embodiment of the disclosure, the above target includes an electroactive substance.

According to an exemplary embodiment of the disclosure, the above electroactive substance includes metal ions or quinone.

According to an exemplary embodiment of the disclosure, the above electroactive substance includes NADH or $H_2O_2$.

According to an exemplary embodiment of the disclosure, the above electrochemical test includes a voltammetric sensing mode.

According to an exemplary embodiment of the disclosure, the immobilized fluorescent materials are physically or chemically confined or localized in a certain defined region of space on the surface of the electrode.

According to an exemplary embodiment of the disclosure, the technique for immobilizing the fluorescent material on the surface of the electrode can be classified by basically two methods, the chemical and the physical method. The former is covalent bond formation dependent and the latter is non-covalent bond formation dependent.

According to the sensing method of the electrochemical sensor of the exemplary embodiment of the disclosure, the target (such as $H_2O_2$ or NADH) undergoes an electrochemical reaction over the electrode surface modified with the above mixture. The sensing sensitivity is enhanced by performing the sensing with the sensing electrode in a light shielding environment.

The disclosure and certain merits provided by the application can be better understood by way of the following exemplary embodiments and the accompanying drawings, which are not to be construed as limiting the scope of the disclosure.

DETAILED DESCRIPTION OF DISCLOSED EMBODIMENTS

Figure 1:
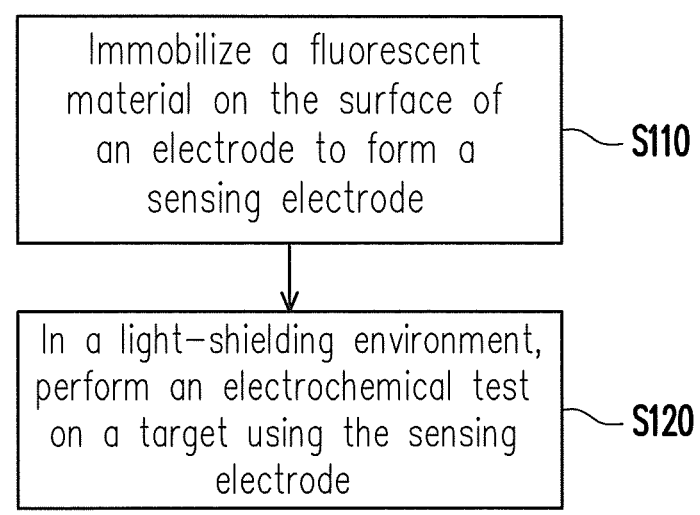
FIG. 1 is a flow chart of steps in an exemplary embodiment sensing process of an electrochemical sensor according to an exemplary embodiment of the disclosure.

FIG. 1 is a flow chart of steps in an exemplary sensing process of an electrochemical sensor according to an exemplary embodiment of the disclosure. First, step 110 is conducted. A fluorescent material is immobilized on the surface of an electrode to form a sensing electrode. The method of immobilizing the fluorescent material on the surface of the electrode can be covalent bond formation dependent or non-covalent bond formation dependent. During the immobilization, materials other than the fluorescent material, such as conductive materials and supporting materials, can be also included if necessary.

In this exemplary embodiment, the fluorescent material includes, for example, quinine hemisulfate, an oligo-chitosan fluorescent derivative, a polyethylene imine fluorescent derivative.

The major source of fluorescence of quinine hemisulfate $(C_{20}H_{24}N_2O_2 \cdot 0.5H_2SO_4 \cdot H_2O)$ is quinine. The structure of quinine is, for example:

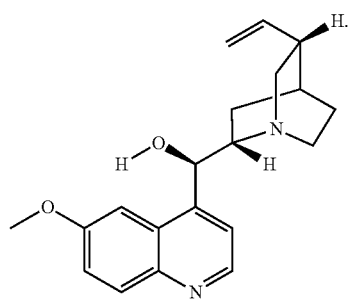

The structure of an oligo-chitosan fluorescent derivative is, for example:

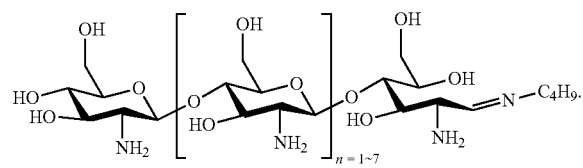

The structure of a polyethylene imine fluorescent derivative is, for example:

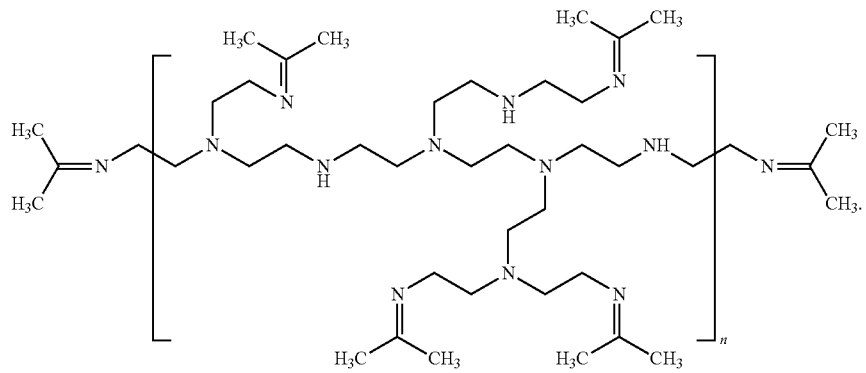

Although the disclosure herein refers to certain illustrated fluorescent materials, such as quinine hemisulfate, an oligo-chitosan fluorescent derivative, a polyethylene imine fluorescent derivative, it is to be understood that these materials are presented by way of example and not by way of limitation. A fluorescent material having an unsaturated bond may fall within the spirit and scope of the fluorescent material of the sensing electrode of the disclosure.

Alternatively speaking, the surface of the sensing electrode is applied with a fluorescent material, which can be immobilized onto the electrode surface via physical or chemical methods. The above fluorescent material includes, for example, quinine hemisulfate, an oligo-chitosan fluorescent derivative, a polyethylene imine fluorescent derivative or other suitable fluorescent materials. Moreover, the material of the electrode on which the conductive composite thin film deposited thereon is not limited. A general electrode having conductive property also can be used here.

Thereafter, step S120 is conducted in a light-shielding environment, in which an electrochemical test is executed on a target using the sensing electrode.

Generally speaking, when a fluorescent material is exposed to an illuminating environment, the electrons of the unsaturated bond in the material are excited and dissipated in a form of light or other energy. Accordingly, the electrochemical test of this exemplary embodiment is performed in a light-shielding environment to mitigate the chances of the fluorescent material on the electrode to be illuminated by light. Therefore, the fluorescent material may catalyze the redox reaction of the electrochemical process or increase the electron transfer rates to further enhance the sensitivity of the sensing process.

The target material may include, for example, NADH or $H_2O_2$. Generally speaking, β-nicotinamide adenine dinucleotide ($NAD^+$) is a coenzyme of dehydrogenase, which serves as an indispensable and critical biochemical substance in a metabolic process. NADH is the reduced product of $NAD^+$ in the reaction of analyte catalyzed by dehydrogenase. NADH can be electrochemically oxidized to its oxidized form, enzymatically active $NAD^+$. In other words, NADH and $NAD^+$ are a redox pair of each other. Based on the electrical current generated by the redox reaction of the redox pair, the change in the concentrations thereof may be determined to further serve as a basis for the sensing evaluation. There are about four hundred dehydrogenases that require $NADH/NAD^+$ as a reaction intermediary in the biochemical reaction. Hence, NADH is widely served as an alternative target (analyte) in the dehydrogenase-based enzymatic biosensors.

Moreover, in an organism, hydrogen peroxide is a product of an oxidase-catalyzed reaction and is also an electroactive substance. Hence, hydrogen peroxide is an important target. For example, the detected target of a glucose sensor, an uric acid sensor and a liver function sensor (GOP, GPT) is the hydrogen peroxide generated by the catalytic reaction of the corresponding oxidase (i.e., glucose oxidase, urate oxidase and glutamate oxidase, respectively). Hence, hydrogen peroxide is an important target for clinical diagnosis.

The target (analyte) in the electrochemical sensing method of the exemplary embodiments of the disclosure is not particularly limited to NADH or $H_2O_2$; any target that is involved in a redox reaction or is an electroactive substance, for example metal ions, quinone, etc., that generates a current change may fall within the scope of the disclosure. In one embodiment of the disclosure, the electrochemical test may adopt a voltammetric sensing mode.

Example 1

The fluorescent material used in the sensing electrode of example 1 is quinine hemisulfate, the electrode is a carbon electrode, and the target is NADH. The execution of Example 1 is disclosed in the following.

The commercially available quinine hemisulfate ($C_{20}H_{24}N_2O_2 \cdot 0.5H_2SO_4 \cdot H_2O$, Fluka) is served as the fluorescent material, wherein the major source of fluorescence is quinine. The chemical structure of quinine is

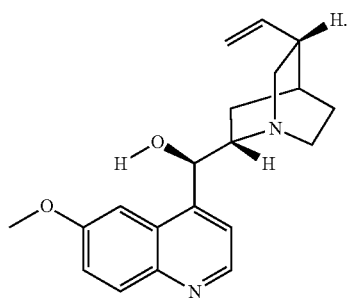

The method for preparing the sensing electrode includes at least the following process steps. First, 100 μl of quinine hemisulfate and 1 mg of acid-washed carbon nanotubes were added to the aqueous solution of Nafion (1%), followed by ultrasonication to obtain a well-dispersed mixture. Thereafter, 2 μl of the mixture was dropped onto the surface of working (carbon) electrode, and heat-dried for 20 minutes. The dropping and drying processes were repeated two more times to obtain a composite thin film of mixture with a total volume of 6 μl. The last drying process took six hours, instead of 20 minutes, to complete the fabrication of the sensing electrode.

The requirements of the detection electrode are disclosed hereinafter. A three-electrode sensing method was used to perform the electrochemical analysis, in which a carbon electrode modified with a fluorescent substance thereon was served as a working electrode, a carbon electrode was served as a counter electrode, and an Ag/AgCl electrode was served as a reference electrode.

The electrochemical assays for NADH were performed in a phosphate buffered saline (PBS) solution at 25° C. in a light-shielding environment and in a non-light-shielding environment, respectively. Amperometric i-t Curves of the modified electrode under various NADH concentrations were measured at 0.12 V (determined from the CV result). The sensing time was maintained for 120 seconds. The assay performed in the light-shielding environment is example 1, while the sensing test performed in the non light-shielding environment is comparative example 1.

Figure 2:
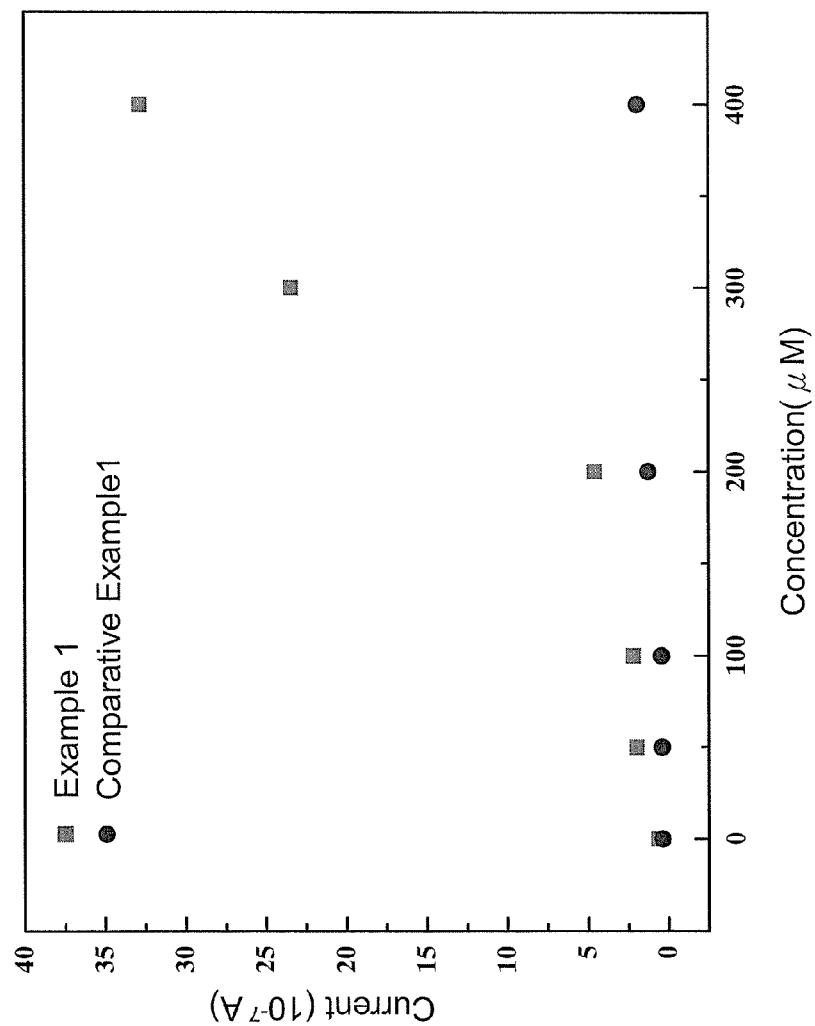
FIG. 2 is a diagram showing the relationships of response current and NADH concentration of example 1 and comparative example 1.

FIG. 2 shows the relationships between response current and NADH concentration of example 1 and comparative example 1. According to FIG. 2, the sensitivity of the sensing curve of example 1 is higher than that of comparative example 1.

Example 2

The fluorescent material used for the sensing electrode of example 2 is an oligochitosan fluorescent derivative, the electrode is a carbon electrode, and the target is NADH. The execution of Example 2 is disclosed herein.

The commercially available oligochitosan, (molecular weight is about 400 to 2000, Lytone Enterprise Inc.) is served as a starting material of the fluorescent material. 75 μl of 1-Butylamine (Aldrich) was added to 50 ml of 1 mg/ml oligochitosan aqueous solution, followed by stirring under 90° C. to react for two days to obtain an oligochitosan fluorescent derivative with an imine group, as shown below.

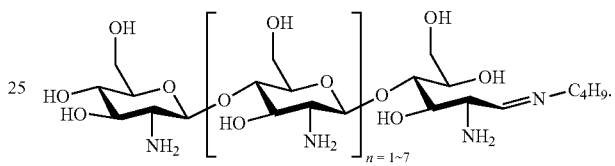

The method for preparing the electrode includes at least the following process steps. First, 100 μl of the oligo-chitosan derivative solution and 900 μl of Nafion (1% aqueous solution) were added to 1 mg of acid-washed carbon nanotubes, followed by ultrasonication to obtain a well-dispersed mixture. Thereafter, 2 μl of the mixture was dropped onto the surface of working (carbon) electrode and heat-dried for 20 minutes. The dropping and drying processes were repeated two more times to obtain a composite thin film of mixture with a total volume of 6 μl. The last drying process took six hours, instead of 20 minutes, to complete the fabrication of the sensing electrode.

The requirements of the detection electrode are disclosed hereinafter. A three-electrode sensing method was used to perform the electrochemical analysis, in which a carbon electrode modified with a fluorescent substance thereon was served as a working electrode, a carbon electrode was served as a counter electrode, and an Ag/AgCl electrode was served as a reference electrode.

The electrochemical assays for NADH were performed in a phosphate buffered saline (PBS) solution at 25° C. in a light-shielding environment and in a non-light-shielding environment, respectively. Amperometric i-t Curves of the modified electrode under various NADH concentrations were measured at 0.12 V (determined from the CV result). The sensing time was maintained for 120 seconds. The assay performed in the light-shielding environment is example 2, while the sensing test performed in the non light-shielding environment is comparative example 2.

Figure 3:
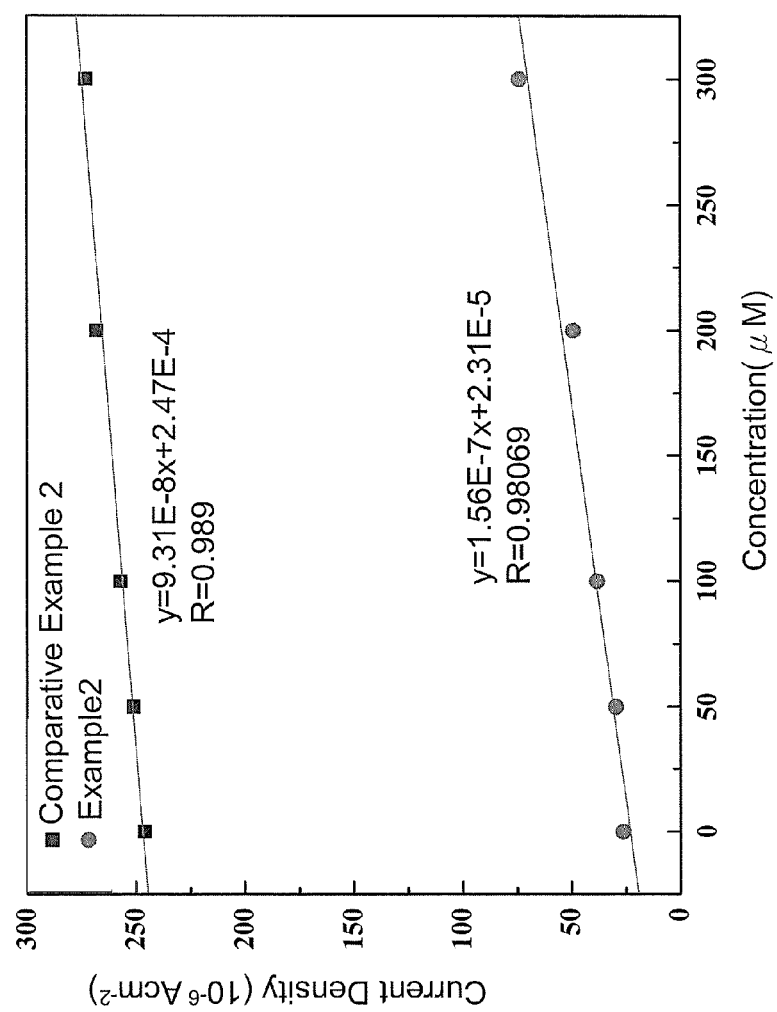
FIG. 3 is a diagram showing the relationships of response current density and NADH concentration of example 2 and comparative example 2.

FIG. 3 shows the relationships between response current density and NADH concentration of example 2 and comparative example 2. According to FIG. 3, the slope of the linear regression equation of the data measured in example 2 is $1.57 \times 10^{-7}$ A/μM, while the slope of the linear regression equation of the data measured in comparative example 2 is $9.31 \times 10^{-8}$ A/μM. According to the above results, the slope measured in example 2 is greater than the slope measured in comparative example 2. Alternatively speaking, under the premise that the sensing concentrations were the same, the electrical current density detected in example 2 is higher; hence a stronger current signal was received. Accordingly, performing example 2 in a light-shielding environment provided a higher sensing sensitivity.

Example 3

The fluorescent material used for the sensing electrode of example 3 is a polyethylene imine (PEI) fluorescent derivative, the electrode is a carbon electrode, and the target is $H_2O_2$. The execution of Example 3 is disclosed herein.

In example 3, the starting material of the fluorescent material is a polyethylene imine (PEI) (average Mw is approximately 1300 by LS, 50 wt. % in $H_2O$, Aldrich). First, 40 ml of acetone (Aldrich) and 2 ml of a polyethylene imine were reacted under 60° C. for two days to obtain a polyethylene imine fluorescent derivative with an imine group, as shown below.

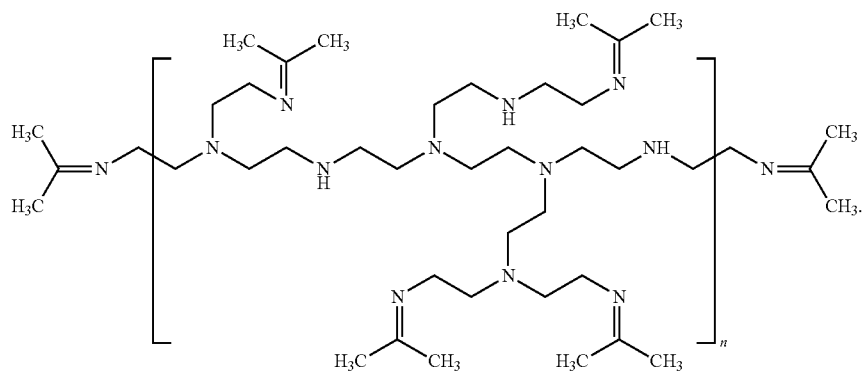

The method for preparing the electrode includes at least the following process steps. 100 μl of the polyethylene imine fluorescent derivative solution and 900 μl of Nafion (1% aqueous solution) were added to 1 mg of acid-washed carbon nanotubes, followed by ultrasonication to obtain a well-dispersed mixture. Thereafter, 2 μl of the mixture was dropped onto the surface of working (carbon) electrode and heat-dried for 20 minutes. The dropping and drying processes were repeated two more times to obtain a composite thin film of mixture with a total volume of 6 μl. The last drying process took six hours, instead of 20 minutes, to complete the fabrication of the sensing electrode.

The electrochemical assays for $H_2O_2$ were performed in a phosphate buffered saline (PBS) solution at 25° C. in a light-shielding environment and in a non-light-shielding environment, respectively. Amperometric i-t Curves of the modified electrode under various $H_2O_2$ concentrations were measured at 0.1V (determined from the CV result). The sensing time was maintained for 20 seconds. The assay performed in the light-shielding environment is example 3, while the sensing test performed in the non light-shielding environment is comparative example 3.

Figure 4:
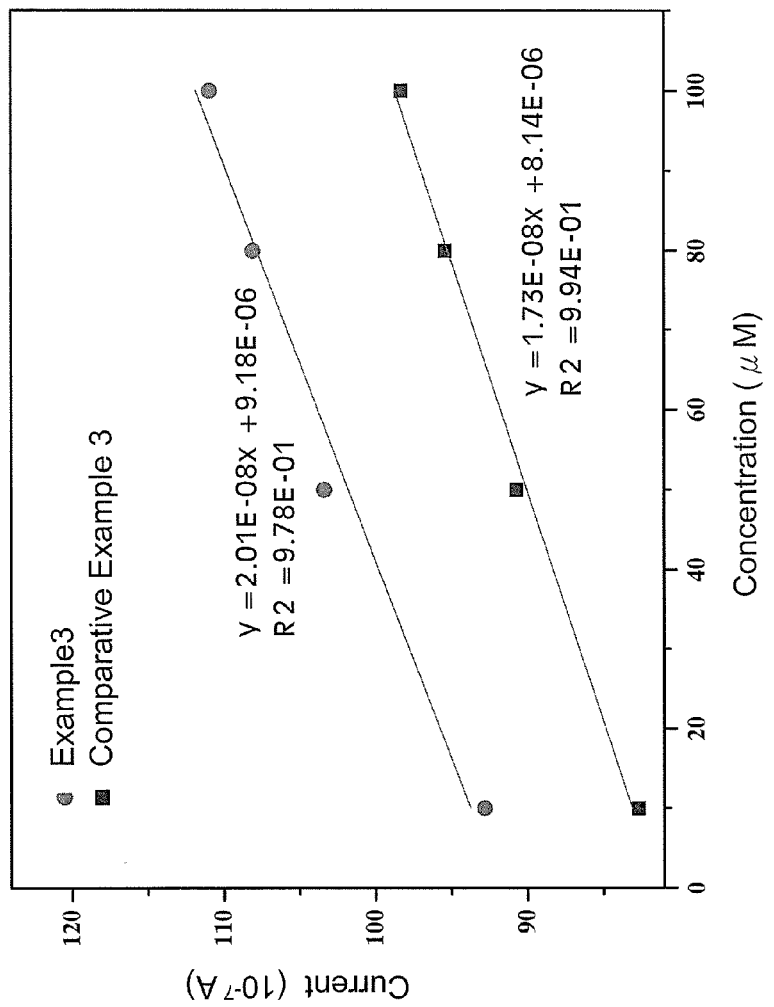
FIG. 4 is a diagram showing the relationships of response current and $H_2O_2$ concentration of example 3 and comparative example 3.

FIG. 4 shows the relationships between response current and $H_2O_2$ concentration of example 3 and comparative example 3. According to FIG. 4, the slope of the linear regression equation of the data measured in example 3 is $2.01 \times 10^{-8}$ A/μM, while the slope of the linear regression equation of the data measured in comparative example 3 is $1.73 \times 10^{-8}$ A/μM. According to the above results, the slope measured in example 3 is greater than the slope measured in comparative example 3. In other words, under the premise that the sensing concentrations were the same, the electrical current detected in example 3 is higher; hence, a stronger current signal was received. Accordingly, performing example 3 in a light-shielding environment provided a higher sensing sensibility.

According to the sensing method of the electrochemical sensor of the exemplary embodiments of the disclosure, a target undergoes an electrochemical reaction over the surface modified with the aforementioned fluorescence material. The current of the redox reaction is increased by subjecting the aforementioned fluorescent material in a light-shielding environment. Ultimately, the sensing sensitivity is enhanced.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A sensing method of an electrochemical sensor, the sensing method comprising:
immobilizing a fluorescent material on a surface of an electrode to form a sensing electrode, wherein the fluorescent material is a material having at least one nitrogen atom;
in a light-shielding environment, using the sensing electrode to perform an electrochemical test on a target.

2. The sensing method of claim 1, wherein the target includes an electroactive substance.

3. The sensing method of claim 2, wherein the electroactive substance includes metal ions or quinone.

4. The sensing method of claim 2, wherein the electroactive substance includes reduced β-nicotinamide adenine dinucleotide (NADH) or hydrogen peroxide ($H_2O_2$).

5. The sensing method of claim 1, wherein the electrochemical test includes a voltammetric sensing mode.

6. The sensing method of claim 1, wherein the technique for immobilizing the fluorescent material on the surface of the electrode includes covalent bond formation dependent or non-covalent bond formation dependent.

7. The sensing method of claim 1, wherein the fluorescent material comprises quinine hemisulfate.

8. The sensing method of claim 1, wherein the fluorescent material comprises an oligochitosan fluorescent derivative.

9. The sensing method of claim 1, wherein the fluorescent material comprises a polyethylene imine (PEI) fluorescent derivative.

* * * * *